United States Patent [19]

Berg

[11] Patent Number: 5,403,448
[45] Date of Patent: Apr. 4, 1995

[54] SEPARATION OF 1-DECENE FROM 2-OCTANONE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 181,049

[22] Filed: Jan. 14, 1994

[51] Int. Cl.$^6$ .......................... B01D 3/36; C07C 7/06
[52] U.S. Cl. ........................................ 203/58; 203/60; 203/62; 203/63; 203/64; 568/410; 585/864; 585/865; 585/866
[58] Field of Search ................. 203/60, 64, 63, 62, 203/58; 568/410; 585/865, 866, 864

[56] References Cited

U.S. PATENT DOCUMENTS

| | | | |
|---|---|---|---|
| 2,305,236 | 12/1942 | Bruson | 568/410 |
| 5,100,515 | 3/1992 | Lee et al. | 203/63 |
| 5,250,157 | 10/1993 | Berg et al. | 568/410 |
| 5,262,015 | 11/1993 | Berg et al. | 585/864 |

*Primary Examiner*—Wilbur Bascomb, Jr.

[57] ABSTRACT

1-Decene is difficult to separate from 2-octanone by conventional distillation or rectification because of the proximity of their boiling points. 1-Decene can be readily separated from 2-octanone by azeotropic distillation. Effective agents are butyl propionate and 1-propanol.

2 Claims, No Drawings

SEPARATION OF 1-DECENE FROM 2-OCTANONE BY AZEOTROPIC DISTILLATION

FIELD OF THE INVENTION

This invention relates to a method for separating 1-decene from 2-octanone using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

In the Fischer-Tropsch process for converting carbon monoxide and hydrogen into liquids, gases and waxes, hundreds of different hydrocarbons and oxygenated compounds are formed, most of them in very small amounts. One valuable compound occuring in reasonable quantities is decene-1, b.p.=173.5° C. When this compound is separated by precision fractionation, all but the closest boiling compounds are separated. The closest boiling ketone is 2-octanone, b.p.=174° C. Azeotropic distillation would be an attractive method of effecting the separation of 1-decene from 2-octanone if agents can be found that (1) will create a large apparent relative volatlity between 1-decene and 2-octanone, and (2) are easy to recover from 1-decene.

1-Decene and 2-octanone boil a degree apart and possess a relative volatility of 1.4. Table 1 shows the relative volatility required to get 99% purity. With no agent, the relative volatility is 1.4 and 37 actual plates are required. With an agent giving a relative volatility of 4.5, only nine actual plates are required.

TABLE 1

Theoretical and Actual Plates Required vs. Relative Volatility for 1-Decene - 2-Octanone Separation

| Relative Volatility | Theoretical Plates Required At Total Reflux, 99% Purity | Actual Plates Required, 75% Efficiency |
|---|---|---|
| 1.4 | 28 | 37 |
| 3.5 | 8 | 11 |
| 4.5 | 6 | 8 |

OBJECTIVE OF THE INVENTION

The object of this invention is to provide a process or method of azeotropic distillation that will enhance the relative volatility of 1-decene from 2-octanone in their separation in a rectification column. It is a further object of this invention to identify organic compounds which in addition to the above constraints, are stable, can be separated from 1-decene in the overhead product and recycled to the azeotrope column and reused with little decomposition.

SUMMARY OF THE INVENTION

The objects of this invention are provided by a process for separating 1-decene from 2-octanone which entails the use of certain organic compounds as the agent in azeotropic distillation.

DETAILED DESCRIPTION OF THE INVENTION

I have discovered that certain organic compounds will greatly improve the relative volatility of 1-decene to 2-octanone and permit the separation of 1-decene from 2-octanone by rectification when employed as the agent in azeotropic distillation.

Table 2 lists the compounds that I have found to be effective. They are ethyl formate, ethyl butyrate, butyl propionate, 2-furaldehyde, 2-methyl-2,4-pentanediol and 1-propanol.

TABLE 2

Effective Azeotropic Distillation Agents For Separating 1-Decene From 2-Octanone

| Compounds | Relative Volatility |
|---|---|
| None | 1.4 |
| Ethyl formate | 3.4 |
| Ethyl butyrate | 7.7 |
| Butyl propionate | 2.25 |
| 2-Methyl-2,4-pentanediol | 2.6 |
| 2-Furaldehyde | 4.6 |
| 1-Propanol* | 2.5 |

*Brings 2-octanone out as overhead

THE USEFULNESS OF THE INVENTION

The usefulness or utility of this invention can be demonstrated by referring to the data presented in Tables 1 and 2. All of the successful agents show that 1-decene can be separated from 2-octanone by means of azeotropic distillation in a rectification column and that the ease of separation as measured by relative volatility is considerable.

WORKING EXAMPLES

Example 1

Twenty grams of 1-decene, 80 grams of 2-octanone and 50 grams of butyl propionate were charged to a vapor-liquid equilibrium still and refluxed for five hours. Analysis indicated a vapor composition of 46.8% 1-decene, 53.2% 2-octanone; a liquid composition of 27.9% 1-decene, 72.1% 2-octanone. This is a relative volatility of 1-decene to 2-octanone of 2.25

Example 2

Twenty grams of 1-decene, 80 grams of 2-octanone and 50 grams of 1-propanol were charged to a vapor-liquid equilibrium still and refluxed for four hours. Analysis indicated a vapor composition of 24.8% 1-decene, 75.2% 2-octanone; a liquid composition of 44.9% 1-decene, 55.1% 2-octanone. This is a relative volatility of 2-octanone to 1-decene of 2.5.

I claim:

1. A method for recovering 1-decene from a mixture of 1-decene and 2-octanone which comprises distilling a mixture of 1-decene and 2-octanone in the presence of an azeotrope forming agent, recovering the azeotrope forming agent and the 1-decene as overhead product and obtaining the 2-octanone from the stillpot, wherein said azeotrope forming agent consists of one material selected from the group consisting of ethyl formate, ethyl butyrate, butyl propionate, 2-methyl-2,4-pentanediol and 2-furaldehyde.

2. A method for recovering 1-decene from a mixture of 1-decene and 2-octanone which comprises distilling a mixture of 1-decene and 2-octanone in the presence of an azeotrope forming agent, recovering the azeotrope forming agent and the 2-octanone as overhead product and obtaining the 1-decene from the stillpot, wherein said azeotrope forming agent is 1-propanol.

* * * * *